(12) United States Patent
Hansen

(10) Patent No.: US 7,645,464 B2
(45) Date of Patent: Jan. 12, 2010

(54) PLANT EXTRACTS

(76) Inventor: Ole Kaae Hansen, Blomstervangen 28, Ega (DK) DK-8250

( * ) Notice: Subject to any disclaimer, the term of this patent is extended or adjusted under 35 U.S.C. 154(b) by 66 days.

(21) Appl. No.: 11/819,066

(22) Filed: Jun. 25, 2007

(65) Prior Publication Data

US 2007/0249517 A1 Oct. 25, 2007

Related U.S. Application Data

(62) Division of application No. 10/519,112, filed as application No. PCT/DK03/00452 on Jun. 30, 2003.

(30) Foreign Application Priority Data

Jun. 28, 2002 (DK) .......................... 2002 00207 U

(51) Int. Cl.
 *A61K 36/00* (2006.01)
 *A61K 36/70* (2006.01)
 *A01N 43/04* (2006.01)
(52) U.S. Cl. ............... 424/725; 514/1; 514/25
(58) Field of Classification Search ........................ None
 See application file for complete search history.

(56) References Cited

U.S. PATENT DOCUMENTS 4,229,483 A * 10/1980 Oura et al. .................. 426/250

FOREIGN PATENT DOCUMENTS

GB 1 510 790 5/1978

GB 1510790 5/1978

OTHER PUBLICATIONS

Noller. Ann Rev Biochem. 1945; 14: 383-406.*
Noller C R. J Ann Biochem. 1945; 14; 383-406.
Vogel, H.C; Tadaro, C. L., Eds. "Fermentation and Biochemical Engineering Handbook-Principles, Process Design and Equipment (2nd Edition)". William Andrew Publishing/Noyes, 1997. pp. 476 and 558.
Thaire Lalitha et al., "Isolation and Properties of Saponins from *Madhuca* Butyracea Seeds", J. Agric. Food Chemistry, vol. 35, pp. 744-748, 1987.
Price et al., "The Chemistry and Biological Significance of Saponins in Foods and Feedstuffs", Critical Reviews in Food Science and Nutrition, vol. 26, No. 1., pp. 27, 75-77, 1987.
Yamahara, et al., "Mi-saponin, Anti-inflammatory Effects of Mi-saponin", vol. 99, No. 6., pp. 612-617, 1979.
Singh, et al., "Chemical Evaluation of Mahua (*Madhuca indica*) Seed", Food Chemistry, pp. 221-228, 1991.
Pompei, et al. "Purificazone delle proteine di soia per ultrafiltrazione-diafiltrazione", La Rivista Italiana Delle Sostanze Grasse, vol. L1, pp. 149-154, 1974.
R.C. Katiyar, Inadequacy of Isolated Mowrin as a Standard for Colorimetric Estimation of Mahua (*Bassia longifolia*) Seed Cake Saponins, Journal of Animal Nutrition, 1998, vol. 6, nr. 3, p. 245-248.
A. Varma, Techniques of removing saponins from Mahua (*Bassia longifolia*) seed cake and its suitability as animal feed, Experientia 35/4, Oct. 12, 1977, Division of Animal Nutrition, Indian Veterinary Research Institute, p. 520-521.

* cited by examiner

*Primary Examiner*—Christopher R Tate
*Assistant Examiner*—Amy L Clark
(74) *Attorney, Agent, or Firm*—Jacobson Holman PLLC

(57) ABSTRACT

The present invention relates to extracts containing beneficial plant secondary metabolites. In particular the present invention relates to plant extracts from butter trees and methods of producing such extracts. Applications of these extracts are furthermore disclosed herein.

10 Claims, No Drawings

PLANT EXTRACTS

This is a divisional application of U.S. Ser. No. 10/519,112 filed Dec. 23, 2004, which is a 371 of PCT/DK03/000452 filed Jun. 30, 2003 of which priority is hereby claimed and which are incorporated by reference into the present application in their entireties.

TECHNICAL FIELD OF THE INVENTION

The present invention relates to plant extracts that comprise plant secondary metabolites. In particular, the present invention relates to plant extracts that comprise saponins and/or their aglycone forms as well as methods of production thereof.

BACKGROUND OF THE INVENTION

Plants produce a vast and diverse assortment of organic compounds, the great majority of which do not appear to participate directly in growth and development. These substances, traditionally referred to as secondary metabolites or plant natural products, often are distributed among limited taxonomic groups within the plant kingdom. The functions of secondary metabolites remain largely unknown, although a number of compounds have been associated with e.g. protection against herbivores and protection against microbial infection, as attractants for pollinators and seed-dispersing animals, and as compounds that influence competition among plant species (allelochemicals).

There is a growing interest in plant natural products, since these products often have a wide range of applications in different kinds of industries, including pharmaceutical industries, cosmetic industries, food industries, detergent industries, etc.

Saponin is an example of a group of plant secondary metabolites. Saponins are glycosylated compounds classified as either triterpenoids, steroids, or steroidal glycoalkaloids. Saponins consist of one or two sugar moieties which are coupled to the aglycon (mono- and bisdesmosides, respectively). Saponins can be hydrolysed to sapogenins and sugar moieties by acid hydrolysis or enzymatic methods. Saponins are water soluble high molecular weight compounds.

Saponins have a wide range of applications. Saponins have the ability of lowering surface tension and the word "saponin" also reflects this as "sapo" is the latin word for soap. Saponins therefore have potential applications in the cosmetic and in the detergent industries. Saponins furthermore have the ability of forming insoluble complexes with cholesterol, which makes some of them suitable for use in the pharmaceutical industry as cholesterol lowering agents. Saponins also have other therapeutical effects. Saponins from chestnut do e.g. possess anti-inflammatory characteristics. Saponins, when injected into the blood stream, are furthermore highly toxic due to their haemolytic properties. Saponins are usually relatively harmless when ingested orally. Steroidal saponins are of great interest owing to their relationship with such compounds as the sex hormones, cortisone, diuretic steroids, vitamin D and cardiac glycosides. Also, saponins are associated with formation of immunostimulating complexes (ISCOMs) (Morein et al., (1995) Clinical Immunotherapeutics 3: 461-475) that are useful in vaccine strategies.

At present however, a major obstacle in exploiting the wide range of potential applications of saponins is the fact that commercially available saponins are relatively expensive.

Commercially available plant extracts containing saponins are e.g. extracts of *Saponaria officinalis*, Quillaia bark and stem, *Castanea sativa* seeds, and extracts of various *Yucca* species. Liquorice root, primula root, and senega root can also serve as raw material for saponin extracts. A problem in this field is that the available sources of saponin extracts are relatively few. And in some cases, e.g. Quillaia bark, the plants are often sparse and expensive because they cannot be cultivated in an efficient manner. Usually the saponins are present in relatively low concentrations. The commercially available saponin extracts are thus often expensive and/or sparse. It should also be noted that the saponins are quite complicated compounds and it has not so far been profitable to develop methods for chemical synthesis of these compounds.

Plant extracts containing saponins and sapogenins are thus of general interest within a wide range of different industries. There is therefore a growing need in the art for alternative sources of saponin extracts and these plant sources should preferably be cheap, easy to obtain, and preferably the saponin content should be relatively high.

For the general description of saponins, extraction, production, and use of saponins reference is made to Ullman's Encyclopedia of Industrial Chemistry (1993), Vol. A23, pp. 485-498. Furthermore, the literature is abundant concerning the extraction, composition and specific effects of the individual saponins derived from plant materials.

The fruits from the butter trees; the African shea tree ((*Bassia*) *Butyrospermum parkii* or *Vitellaria paradoxa*) and Indian butter tree (*Bassia latifolia* and *B. longifolia*; or *Madhuca Sp.*) of the *Sapotacea* family contain seeds (nuts) that are suitable for extraction and production of butter fat. Shea butter fat and Indian butter fat have a wide range of applications including as food, food ingredient, emulsifier, and also as an ingredient in the production of cosmetics.

Extraction and production of butter fat leaves a press cake or an extracted residue (meal) as a by-product (waste product). It has proven difficult to find normal outlets for this by-product as an ingredient in e.g. animal feed. This is probably due to a content of secondary metabolites that are toxic to mammals. Consequently the material is presently disposed off by e.g. burning.

An investigation of an alcohol extract from "mowrah meal" from the Indian butter tree Bassia latifolia as well as other related species revealed presence of a novel triterpene sapogenin called "bassic acid" ($C_{30}H_{46}O_5$) (Heywood et al., J. Chem. Soc. (1939), Part V, pp. 1124-1129). Bassic acid from *B. butyrace* was extracted with a solution containing 5% hydrochloric acid. Bassic acid was also identified in the by-product from shea tree. It is disclosed that saponins and sapogenins can be extracted from by-products by water or alcohol extraction. The document does not disclose any methods of stabilising the saponins in the watery solution from undergoing hydrolysis. Likewise, no possible applications of the extracts are disclosed herein and consequently no companies have been encouraged to exploit by-products for production of saponin/sapogenin extracts on basis of this study published in 1939.

OBJECT OF INVENTION

One object of the present invention is to find a useful application, other than e.g. burning, of by-products from the production of shea butter fat and mowrah fat.

It is furthermore an object to provide methods of producing low-cost and high-quality saponin/sapogenin containing extracts. It is of especially importance to provide a chemically stable environment during manufacture and storage of the extract. And also to provide an environmentally friendly production method of said extracts.

Another object is to identify applications of butter tree extracts according to the invention.

SUMMARY OF THE INVENTION

The object of the present invention is achieved by a method of preparing an aqueous extract comprising saponins on basis of waste product from a butter tree of the Sapotacea family, said method comprising the following steps:
(i) mixing one part waste product with 4-30 parts of water;
(ii) incubating the mixture formed in step (i) under alkaline conditions; and
(iii) recovering an aqueous extract comprising saponins by removing solids from the alkaline mixture formed in step (ii).

The invention further relates to various uses of such extracts as well as to extracts prepared by the methods herein.

Definitions

"Butter tree": As used herein butter tree can be a shea butter tree, preferably (*Bassia*) *Butyrospermum parkii*, or an Indian butter tree (preferably *Bassia latifolia* or *B. longifolia*; sometimes referred to as *Madhuca sp.*) of the *Sapotacea* family.

"By-product": As used herein a by-product refers to the by-product from production of butter fat from shea butter tree or Indian butter tree. The terms "by-product", "waste-product", "butter cake meal", "press cake", "extracted residue", etc. are used interchangeably. The by-product may be virtually fat free or there may be considerable amounts of residual fat depending on the method of extraction.

"Saponins": Saponins are glycosylated compounds found in many plants classified as either triterpenoids, steroids, or steroidal glycoalkaloids. Saponins consist of one or two sugar moieties which are coupled to the aglycon. Saponins can be hydrolysed to sapogenins and the corresponding sugar moieties by acid hydrolysis or enzymatic methods "Water": Water according to the present invention refers to any aqueous solution, preferably in the form of pure or essentially pure water such as e.g. distilled water or tap water. Water can also refer to an aqueous solution comprising an alkaline substance or an alkaline buffer.

"Alkaline conditions": Extraction of butter tree waste product according to the present invention is carried out under alkaline conditions, i.e. the pH-value during the extraction process must be at least 7. The alkali constituent can be in the form of an alkaline substance or an alkaline buffer. The alkali constituent can be added to the water prior to mixture with butter tree waste product or it can be added after water has been mixed with the waste product. The alkali can be any substance with the ability to raise pH to a level of above 7. Examples of alkali substances include but are not limited to: NaOH, KOH, $Ca(OH)_2$, LiOH, $NH_3$, $Mg(OH)_2$, ammonium hydroxide, potassium-, sodium-, calcium-, ammonium-, or hydroxide carbonate.

DETAILED DESCRIPTION OF THE INVENTION

In the present invention it is disclosed that water based plant extract from butter tree by-product comprises saponins and/or sapogenins and have a wide range of applications. Methods of production of such extracts are furthermore disclosed herein.

In abovementioned applications the extract may be purified and have a content of saponins and/or sapogenins or their derivatives in a concentration of min. 5% by weight calculated as sapogenins. This is especially the case in pharmaceutical as well as food applications and in a variety of cosmetic products. But in some applications there is no need for any special purification of the extract e.g. agricultural use. In some cases it is even beneficial that the extract has its normal content of tannins, e.g. in special skin care products or in leather tanning.

The normal procedure for extracting saponins and sapogenins involves use of an organic solvent such as e.g. alcohol or an alcohol/water. The methods disclosed in the present application employ water based extraction methods that are both efficient and environmentally friendly.

The evaporation of water can take place at atmospheric or reduced pressure, by spray drying or any standard processing method known by people skilled in the art.

The extract obtained so far is composed of a diversity of water soluble types of constituents. One group is the tannins. The tannins are a group of simple and complex phenol, polyphenol and flavonoid compounds, bound with starches, and often they are just classified as tannins simply as they contain variations on gallic acid. One simple way of fractionating the constituents is by applying ultra filtration to separate the constituents according to their molecular size.

Extracts obtained by the methods of the invention may be further subjected to a hydrolysing step converting a fraction of the saponins to their corresponding sapogenins. The sapogenin part may be further purified by recrystallisation and/or derivatised with fatty moieties to make it soluble in e.g. oil.

In a preferred embodiment of the invention the plant extract obtained by the process from *Butyrospermum parkii* or *Bassia sp.* is further characterised by a content of saponin and/or sapogenin or their derivatives of min. 5% by weight calculated as sapogenin.

In a first aspect of the present invention a method is disclosed wherein an aqueous saponin extract from a butter tree waste product is produced, said method comprising the following steps:
(i) mixing one part waste product with 4-30 parts of water;
(ii) incubating the mixture formed in step (i) under alkaline conditions; and
(iii) recovering an aqueous extract comprising saponin by removing solids from the alkaline mixture formed in step (ii).

The aqueous extraction is carried out by mixing water with waste product in step (i). One part of waste product is preferably mixed with 7-25 parts of water, more preferably 10-20 parts of water, and even more preferably 15-20 parts of water.

The alkali conditions in step (ii) are obtained by addition of an alkali in the form of a base and/or buffer. Addition of the alkali component raises the pH to a level of between 7-14, preferably 7-10, more preferably 7-9 and most preferably 7-8.

Incubation in step (ii) can be performed at any temperature of between 15 and 95° C., e.g. at 15, 20, 25, 30, 35, 40, 45, 50, 55, 60, 65, 70, 75, 80, 85, 90, or 95° C. at a period of between 5 minutes and 5 hours, e.g. 5, 10, 15, 20, 25, 30, 35, 40, 45, 50, 55, 1 hour, 2 hours, 3 hours, 4 hours, and 5 hours.

Separation of solid components in step (iii) can take place by filtration or centrifugation. Examples of suitable filters include: plate, frame, and vacuum filters, that are preferably precoated with e.g. diatomaceous earth.

In order to ensure keepability one or more preservative agents such as benzoates or sorbates may be added.

Furthermore, the extract obtained in step (iii) can be further concentrated and/or purified by evaporation of water and/or by ultrafiltration and/or by recrystallisation.

In a preferred embodiment, an extract obtained by means of the methods disclosed herein is subsequently enriched with sapogenins by subjecting the extract to partly or complete hydrolysis, by means of acids or enzymes and thereby obtaining an extract enriched with sapogenins. The sapogenins may be further purified by recrystallisation. Furthermore, the saponins and/or the sapogenins of an extract according to the invention can also be chemically modified by e.g. derivatising with fatty moieties in order to increase oil solubility.

Extracts according to the present invention do have a number of different applications:
- as a food additive and/or food ingredient;
- as an ingredient in a detergent product;
- as an ingredient in a cosmetic product;
- as an active component in a pharmaceutical product for topical application;
- as an active component in a pharmaceutical product for lowering the level of serum cholesterol in a human being or in other mammals;
- as an active compound in a pharmaceutical product for treatment of inflammatory diseases;
- as an active compound in a pharmaceutical product for systemic administration, e.g. treatment of cardiac disorders or diuretic disorders, or vitamin D associated disorders;
- as an active component in the manufacture of a nutritional supplement;
- as an ingredient in immunostimulatory complexes (IS-COMs).

The plant extract e.g. may be used as a wetting agent or emulsifier. The extract can be used as a wetting agent in many applications e.g. spraying of pesticides and herbicides, dust control, etc. Furthermore it can be formulated with other surfactants, builders and ingredients normally used in detergents.

As to acceptable cosmetic ingredients, reference is made to handbooks covering geographical areas e.g. International Cosmetic Ingredient Directionary and Handbook published by The Cosmetic, Toiletry, and Fragrance Association. An acceptable pharmaceutical ingredient is to be understood as the ingredients and exipients monographed in any national or regional pharmacopoeia e.g. European Pharmacopoeia.

As for the food products, reference is made to the WHO/FAO listing of acceptable animal and plant derived ingredients.

The invention is illustrated in the following non-limiting examples:

EXAMPLES

Example 1

Use of a Shea Extract as a Wetting Agent and Emulsifier 1.1 Production of the Extract 300 g defatted shea meal by-product was mixed with 6000 ml tap water. pH of this meal solution is neutral. pH was then elevated by addition of 6 g sodium carbonate (2 weight-% of the meal). Without addition of alkaline, the saponins will gradually hydrolyse and pH of the solution will also gradually decrease. The extract was then incubated at 80° C. for 15 minutes and subsequently filtered. The resulting brown coloured extract had a content of dry matter of 2.1% by weight. The extract was diluted to a content of 2% dry solid matter 0.02% Kathon CG (preservative) was added. The extract is named SHEX-2 in the following.

1.2. Surface Tension Properties of SHEX-2

TABLE 1

Surface tension at different concentrations

| Parameter | Concentration in g/l | Surface tension at 22° C. in dyn/cm |
|---|---|---|
| SHEX-2, undiluted | 20 | 49.1 |
| SHEX-2, 1:10 | 2 | 56.1 |
| SHEX-2, 1:100 | 0.2 | 60.7 |
| SHEX-2, 1:1000 | 0.02 | 72.0 |
| Distilled water | 0 | 72.4 |

The measured surface tensions illustrate that the crude extract functions as a wetting agent and surfactant at concentrations of dry solid matter of 0.2-20 g/l.

1.3 Interfacial Tension

The interfacial tension between soya oil and SHEX-2, 1:10 (2 g/l) was <5 dyn/cm. This illustrates the emulsifying properties of the extract.

1.4 Use of SHEX-2 as a Defattinq Agent

A test person with hands oiled by normal salad oil rubbed 10 ml. of SHEX-2 in. By rinsing with water an emulsion was formed and after drying no traces of oil was left on the hands.

Example 2

Use of a Shea Extract as a Cosmetic Ingredient

SHEX-2 was tested in the following shampoo formulation:

| | |
|---|---|
| SHEX-2 | 25.0% |
| Nyfamid KDK (Cocoa fatty acid diethanol amide) | 5.5% |
| Guardan 178 (Guar gum) | 1.3% |
| Drom 7699 (Fragrance) | 0.5% |
| Demineralised water | ad. 100.0% |

A test of abovementioned formulation showed that SHEX-2 is suited as a cosmetic ingredient in a hair shampoo in combination with other normal cosmetic ingredients.

Example 3

Use of a Purified and Concentrated Shea Extract as an Ingredient in a Therapeutic Skin Tonic 3.1 Data Profile for SHEX-14:

The crude extract from example 1 was further purified and concentrated to form an extract named SHEX-14. The product had the following properties:

| | |
|---|---|
| Appearance: | Clear, yellowish liquid |
| Dry solid content: | 14% by weight |
| Specific gravity (20° C.): | 1.055 g/ml |
| Surface tension (20° C.): | 46.5 dyn/cm |

3.2 Composition of the Skin Tonic:

SHEX-14 was formulated into the following skin tonic product:

| | | |
|---|---|---|
| SHEX-14 | 50% | |
| Glycerine B.P. | 15% | |
| Demineralised water | 35% | |

The product was tested on skin areas with atopic eczema. The product was applied once daily on damp skin after showering. After one week there was a clear improvement of the eczema; reduced scaling and a reduction of inflammatory redness.

Example 4

Use of a Concentrated and Purified Shea Extract as an Ingredient in a Food Product SHEX-14 was used as a foam stabiliser in a concentrated soft drink. "Fruiss Grenadine" (Rutin s.a., France) was selected as the test soft drink as it is formulated without foam additives and has no ability to foam. The concentrated soft drink was added varying amounts of SHEX-14. The samples were diluted with water (1:9) to normal use concentration and transferred to glass cylinders fitted with glass stoppers. After shaking the cylinders they were left for observation of the foam stability. At a concentration of SHEX-14 of 56 g dry matter pr. 100 liter of soft drink the creamy foam ring had a stability of more than 30 minutes.

Example 5

Yield of Shea Extract at Different Meal/Water Ratios

The following table show the yield of dry matter in the shea extract at extractions performed at different meal/water ratios. The extractions were performed at 80° C. for 15 minutes at a pH in the interval 7-8. As in example 1, pH was adjusted by the addition of 6 g of sodium carbonate (2 weight-% of the meal).

TABLE 2

| Parameter | Ratio - 1:20 | Ratio - 1:10 | Ratio - 1:5 |
|---|---|---|---|
| Weight of shea meal in g | 300 | 300 | 300 |
| Volume of water in ml | 6000 | 3000 | 1500 |
| Yield of extract in g | 3170 | 1266 | 197 |
| Dry matter in extract in % by weight | 2.1 | 3.0 | 5.7 |
| Extracted dry matter in g | 66.6 | 38.0 | 11.2 |
| Yield of dry matter in % by weight of meal | 22.2 | 12.7 | 3.7 |

According to table 2, the dry matter yield is strongly dependent on the extraction ratio. A ratio in the range of 1:4 to 1:30 will yield crude extracts with contents in the range from 6 to 1.5% by weight of dry matter. The ratio used in an actual production procedure is dependent on the intended use of the extract (e.g. as is or for further purification) as well as the intended use of the extracted meal residue (e.g. for feedstuffs or for biogas production).

Example 6

Shea Extract Modified by Hydrolysis

5% sulphuric acid by weight was added to SHEX-14 extract and the mixture was subsequently hydrolysed for 18 hours at 95° C. The precipitate was washed with alcohol and dried. The resulting sapogenin enriched extract appeared as a dark coloured, waxy substance in a yield of 5% by weight of the dry matter of SHEX-14.

Example 7

Tablet Containing Hydrolysed Shea Extract 100 mg tablets containing 20 mg hydrolysed extract from example 6 were formulated as follows:

| | | |
|---|---|---|
| Active compound: | SHEX-hydrolysed | 20 mg |
| Excipients: | Maize starch | 40 mg |
| | Lactose | 26 mg |
| | Polyvinylpyrrolidone | 5 mg |
| | Silica powder | 3 mg |
| | Carboxymethyl starch | 3 mg |
| | Magnesium stearate | 2 mg |
| | Talc | 1 mg |

The invention claimed is:

1. A concentrated or purified preparation obtained from an aqueous extract of the shea butter tree (*Butyrospermum parkii*) comprising saponins, obtained by the process of:
   (i) mixing one part by weight of butter cake meal from a shea butter tree (*Butyrospermum parkii*) with 4-30 parts by weight of water;
   (ii) incubating the mixture formed in step (i) under alkaline conditions (pH>7) to form an alkaline mixture;
   (iii) removing solids from the alkaline mixture formed in step (ii) to yield an aqueous extract containing saponins; and
   (iv) concentrating and/or purifying the aqueous extract obtained in step (iii) by evaporation of water and/or ultrafiltration and/or crystallization.

2. The preparation of claim 1, wherein said extract contains at least 1% by weight of dry matter.

3. The preparation of claim 1, wherein the concentrated or purified product of step (iv) is subjected to hydrolysis to convert a fraction of the saponins to their corresponding sapogenins.

4. A method of using the preparation of claim 1 in a detergent, comprising:
   adding the preparation of claim 1 to a detergent composition; thereby producing a detergent product.

5. A method of extracting saponins from butter cake meal from a shea butter tree (*Butyrospermum parkii*) comprising:
   (i) mixing one part by weight of butter cake meal with 4-30 parts by weight of water;
   (ii) incubating the mixture formed in step (i) under alkaline conditions (pH>7) to form an alkaline mixture;
   (iii) removing solids from the alkaline mixture formed in step (ii) to yield an aqueous extract containing saponins; and wherein the aqueous extract obtained in step (iii) is further concentrated and/or purified by evaporation of water and/or ultrafiltration and/or crystallization.

6. The method according to claim 5, wherein the alkaline conditions are obtained by addition of an alkali in the form of a base and/or an alkaline buffer.

7. The method according to claim 5, wherein the incubation step (ii) is performed at a pH of >7 to 10.

8. The method according to claim 5, wherein the incubation step (ii) is performed over a temperature of between 15° C. and 95° C. at a period of between 10 minutes and 5 hours.

9. The method according to claim 5, wherein the solids are removed from the extract in step (iii) by filtration or centrifugation.

10. The method according to claim 5, yielding an extract containing at least 1 weight % dry matter.

* * * * *